US005578735A

United States Patent [19]
Vandenbossche et al.

[11] Patent Number: 5,578,735
[45] Date of Patent: Nov. 26, 1996

[54] PROCESS FOR THE PREPARATION OF INDOLE COMPOUNDS FROM N-PROTECTED INDOLINES

[75] Inventors: Jean J. Vandenbossche; Herve Borowiak, both of Sevran; Alain LaGrange, Coupvray, all of France

[73] Assignee: L'Oreal, Paris, France

[21] Appl. No.: 547,732

[22] Filed: Oct. 26, 1995

[30] Foreign Application Priority Data

Oct. 27, 1994 [FR] France ................................. 94 12892

[51] Int. Cl.$^6$ ................................................ C07D 209/10
[52] U.S. Cl. ................................................ 548/491
[58] Field of Search ................................................ 548/491

[56] References Cited

PUBLICATIONS

Kiguchi, et al. "One–Pot Synthesis of Indoles from 1–Benzyl–2,3–dihydroindoles" Syntheisis, 1989, pp. 778–781.
Bajwa, "One–Pot Transformation of Benzyl Carbamates into t–Butyl Carbamates", Terahedron Letters, vol. 33, No. 21, 1992, pp. 2955–2956.
Felix, et al. "Rapid Removal of Protecting Groups from Peptides by Catalytic Transfer Hydrogenation with 1,4–Cyclohexadiene" J. Org. Chem., vol. 43, No. 21, 1978.
Kametani et al., Studies on the Syntheses of Heterocyclic Compounds. Part 865.[1] A Novel Synthesis of Indole Derivatives by Intramolecular Nucleophilic Aromatic Substitution, J. C. S. Perkin 1, 1981, pp. 290–294.
Jackson, "Rapid Selective Removal of Benzyloxycarbonyl Groups from Peptides by Catalytic Transfer Hydrogenation", Synthesis, 1976, pp. 685–687.

Primary Examiner—Joseph McKane
Attorney, Agent, or Firm—Finnegan, Henderson, Farabow, Garrett and Dunner, L.L.P.

[57] ABSTRACT

The present invention relates to a novel process for the preparation of indole compounds of the formula II:

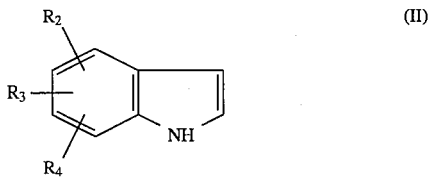

from N-protected indolines of the formula I.

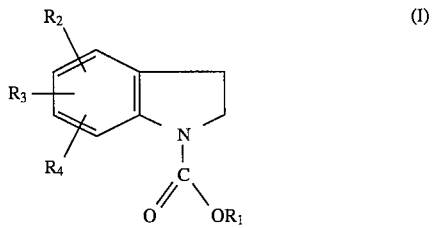

16 Claims, No Drawings

PROCESS FOR THE PREPARATION OF INDOLE COMPOUNDS FROM N-PROTECTED INDOLINES

The present invention relates to a new process for the preparation of indole compounds from N-protected indolines.

Indole and derivatives thereof are starting materials widely used in the dye, cosmetics, pharmaceutical and food industries. Indole is, in particular, one of the starting materials which may be used for the synthesis of tryptophan, an amino acid essential in nutrition.

Indoles are generally synthesized in several long and expensive steps. Furthermore, this synthesis requires steps of forced oxidation, at high reaction temperatures, often above 140° C., which can be hazardous.

The article by Kametani et al., J.C.S. Perkin 1,290–294, 1980, the disclosure of which is incorporated herein by reference, describes the synthesis of indole derivatives in two steps, starting with N-protected indolines which are oxidized and are then deprotected in order to obtain the corresponding indole.

The article by Kiguchi et al., Synthesis, 778–781, 1989, the disclosure of which is incorporated herein by reference, describes the preparation of indole compounds in a single step, by simultaneous debenzylation and oxidation of 1-benzyl-2,3-dihydroindolines, in the presence of a catalyst, in a basic medium. This process has the advantage of consisting of only a single step. But this article mentions that 3 to 15% of the indoles obtained are N-protected by the benzyl group, a result unsatisfactory in industrial terms.

During efforts directed towards overcoming these problems, the inventors discovered the process which forms the subject of the invention.

The subject of the present invention is thus a novel process for the preparation of indole compounds in a single step, characterized in that it comprises contacting, in the presence of a hydrogenation catalyst, an N-protected indoline of the following formula (I):

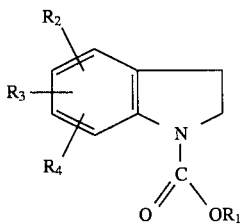

(I)

in which:

$R_1$ represents a linear or branched, substituted or unsubstituted $C_2$–$C_{10}$ alkenyl radical, or a substituted or unsubstituted benzyl group;

$R_2$, $R_3$ and $R_4$, which may be identical or different, represent a hydrogen atom, a halogen atom such as bromine, chlorine, fluorine or iodine, or a $C_1$–$C_7$ alkyl, aryl, hydroxyl, $C_1$–$C_7$ alkoxy, $C_3$–$C_7$ alkenyloxy, aryloxy, acyloxy, formyl, aroyl, hydroxymethyl, arylhydroxymethyl, carboxyl, alkoxy($C_1$–$C_7$)carbonyl, carbamoyl, amino, monoalkyl($C_1$–$C_7$)amino, dialkyl($C_1$–$C_7$)amino, alkoxy($C_1$–$C_7$)carbonylamino, acylamino, N-alkyl($C_1$–$C_7$)acylamino, dialkyl($C_1$–$C_7$)formamidino, or dialkoxy($C_1$–$C_7$)methyl radical; with hydrogen or a hydrogen donor, the contacting being carried out with stirring, in a solvent medium, at a pH less than or equal to 7 and at a temperature ranging from room temperature to the reflux temperature of the contacting medium, to obtain an indole compound of formula

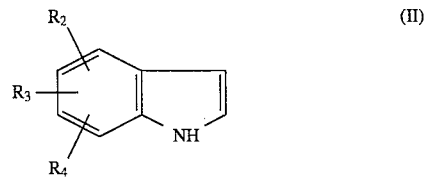

(II)

in which $R_2$, $R_3$, and $R_4$ have the same meanings as in formula (I).

According to this process, N-protected indole compounds are essentially not formed, and this represents an advantage in terms of the purity of the final product obtained and the reaction yield with regard to this product. Preferably, less than 3% N-protected indoles are formed.

In formulae (I) and (II) above, the term aryl preferably denotes a phenyl group or a phenyl group bearing one or more substituents chosen from a halogen atom, a trifluoromethyl radical, a $C_1$–$C_7$ alkyl or $C_1$–$C_7$ alkoxy radical, or a nitro, amino, alkyl($C_1$–$C_7$)amino or dialkyl($C_1$–$C_7$)amino group.

The acyl radical preferably denotes an alkanoyl radical derived from an aliphatic carboxylic acid having from 1 to 7 carbon atoms, such as the formyl, acetyl, or propionyl groups, or an aroyl group derived from an aromatic carboxylic acid, such as the benzoyl group.

The alkenyloxy radical preferably denotes an allyloxy radical.

The starting indolines of formula (I) are known products which may be prepared, for example, according to the process described in French patent application FR-A2,699, 532, the disclosure of which is incorporated herein by reference.

Preferably, the indolines of formula (I) may be:

5,6-dihydroxy-1-N-benzyloxycarbonylindoline, 5,6-dihydroxy-1-N-allyloxycarbonylindoline, 6-hydroxy-1-N-benzyloxycarbonylindoline, 4-hydroxy-5-methoxy-1-N-benzyloxycarbonylindoline, 6-hydroxy-7-methoxy-1-N-benzyloxycarbonylindoline, 5-methoxy-6-hydroxy-1-N-benzyloxycarbonylindoline, and 1-N-benzyloxycarbonylindoline.

Preferably, the indole compounds of formula (II) may be 5,6-dihydroxyindole, 6-hydroxyindole, 4-hydroxy-5-methoxyindole,6-hydroxy-7-methoxyindole,5-methoxy-6-hydroxyindole, and indole.

According to a preferred embodiment of the process according to the invention, the pH of the solvent medium ranges from 5 to 7 and, more preferably, from 6.5 to 7.

The hydrogen used according to the process of the invention is preferably molecular hydrogen at a low pressure, more preferably at a pressure in the range of 1 to 5 atmospheres.

Preferably, the hydrogen donors are olefinic hydrogen donors such as, for example, cyclohexene, substituted cyclohexenes, 1,3-cyclohexadiene and 1,4-cyclohexadiene.

According to the process of the invention, any suitable hydrogenation catalyst may be used. The catalyst may be a metal chosen from chromium, molybdenum, tungsten, platinum, palladium, rhodium, cobalt, nickel and ruthenium, oxides thereof, or combinations of these substances. Examples of these oxides and combinations are cobalt oxide, molybdenum oxide, and cobalt molybdate.

The preferred hydrogenation catalysts are palladium, and Raney nickel, as well as other metals from the platinum group, such as platinum, platinum-on-charcoal, or soluble complexes of platinum. The catalyst may be deposited, in a known manner, on an inert support of neutral pH, thereby not influencing the pH of the reaction solvent medium. These inert supports may be, for example, neutral wood charcoal, neutral charcoal, neutral alumina, zeolites, and clays. Neutral charcoal is preferably used.

The hydrogenation catalysts are generally present in an amount in the range of 0.2 to 5% by weight in terms of metal equivalent relative to the weight of the compound of formula (I) to be reacted.

The solvent used is advantageously an inert solvent selected from, for example, a $C_1$–$C_4$ alcohol, such as methanol or ethanol, a hydrocarbon, such as benzene or toluene, ethyl acetate, dimethylformamide, or mixtures thereof. The solvent used is preferably ethanol or ethyl acetate.

When the reaction is complete, the expected products such as the indole, may, if necessary, be recovered by methods which are well-known in the state of the art, such as crystallization, distillation, or vapor entrainment.

The products obtained according to the process of the invention, that is to say the indole compounds of formula (II) including indole, may be used for various purposes, including as intermediates in the preparation of compounds, such as amino acids, alkaloids, and tryptamines, or as finished products in any type of chemical, cosmetics, food or pharmaceutical industry, or the like.

The following examples are intended to illustrate the invention without, however, limiting the scope thereof.

EXAMPLES

Example 1

Synthesis of 5,6-dihydroxyindole

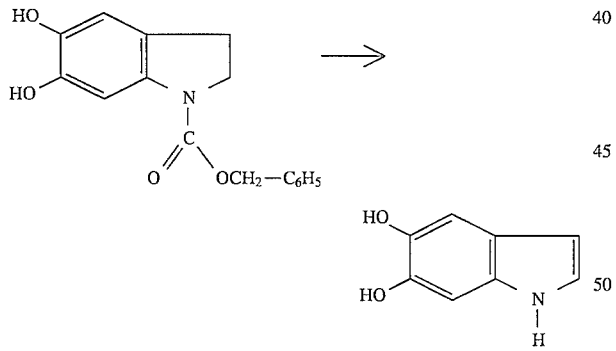

11.4 g of benzyl 5,6-dihydroxy-2,3-dihydroindole-1-carboxylate, 60 ml of ethanol, 5.7 g of 10% palladium-on-charcoal, 5.7 ml of water and 23 ml of cyclohexene were mixed together, and the mixture was maintained at reflux for one hour.

The catalyst was filtered off at room temperature, and the solution was then evaporated to dryness. The beige-colored residue was taken up in hot isopropyl ether in the presence of charcoal and then filtered while hot, and the organic phase was evaporated. 4.5 g of a light beige solid were obtained (expected product), the melting point of which is 144° C., and the elemental analysis of which for $C_8H_7NO_2$ is as follows:

|  | C | H | N | O |
|---|---|---|---|---|
| Calculated | 64.42 | 4.73 | 9.39 | 21.45 |
| Found | 64.20 | 4.91 | 9.41 | 21.44 |

Example 2

Synthesis of 6-hydroxyindole

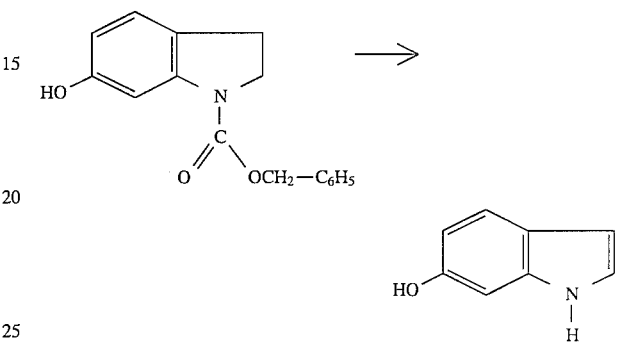

The process described in Example 1 above was used, starting with 5.4 g of benzyl 6-hydroxy-2,3-dihydroindole-1-carboxylate.

2 g of white crystals were obtained (expected product), the melting point of which is 130? C. and the elemental analysis of which for $C_8H_7NO$ is:

|  | C | H | N | O |
|---|---|---|---|---|
| Calculated | 72.17 | 5.30 | 10.52 | 12.02 |
| Found | 72.18 | 5.31 | 10.49 | 11.99 |

We claim:

1. A process for preparing an indole compound comprising a single step of contacting, in the presence of a hydrogenation catalyst, an N-protected indoline of the formula (I):

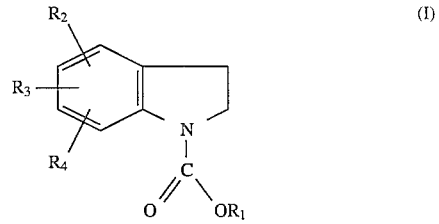

wherein:

$R_1$ represents a linear or branched, substituted or unsubstituted $C_2$–$C_{10}$ alkenyl radical, or a substituted or unsubstituted benzyl group;

$R_2$, $R_3$, and $R_4$, which may be identical or different, represent a hydrogen atom, a halogen atom, or a $C_1$–$C_7$ alkyl, aryl, hydroxyl, $C_1$–$C_7$ alkoxy, $C_3$–$C_7$ alkenyloxy, aryloxy, acyloxy, formyl, aroyl, hydroxymethyl, arylhydroxymethyl, carboxyl, alkoxy($C_1$–$C_7$)carbonyl, carbamoyl, amino, monoalkyl($C_1$–$C_7$)amino, dialkyl($C_1$–$C_7$)amino, alkoxy($C_1$–$C_7$)carbonylamino, acylamino, N-alkyl($C_1$–$C_7$)acylamino, dialkyl($C_1$–$C_7$)formamidino, or dialkoxy($C_1$–$C_7$)methyl radical, with hydrogen or a hydrogen donor, said contacting being carried out with stirring, in a solvent medium, at a pH less than or equal to 7 and at a temperature ranging from room temperature to the reflux temperature of the contacting medium to obtain an indole compound of the formula (II):

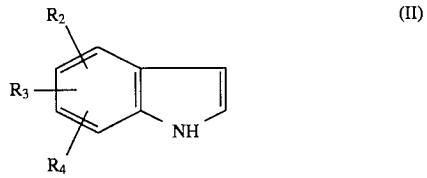
(II)

wherein $R_2$, $R_3$, and $R_4$ are defined as above.

2. The process according to claim 1, wherein the aryl radical denotes a phenyl group unsubstituted or substituted with at least one substituent, said substituent being a halogen atom, a trifluoromethyl radical, a $C_1$–$C_7$ alkyl or $C_1$–$C_7$ alkoxy radical, or a nitro, amino, alkyl($C_1C_7$)amino or dialkyl($C_1$–$C_7$)amino group, the acyl portion of said acyloxy, acylamino, or N-alkyl($C_1$–$C_7$)acylamino radical denotes an alkanoyl radical derived from an aliphatic carboxylic acid having from 1 to 7 carbon atoms or an aroyl group derived from an aromatic carboxylic acid, and the alkenyloxy radical denotes an allyloxy radical.

3. The process according to claim 1, wherein said N-protected indoline of formula (I) is 5,6-dihydroxy-1-N-benzyloxycarbonylindoline, 5,6-dihydroxy-1-N-allyloxycarbonylindoline, 6-hydroxy- 1-N-benzyloxycarbonylindoline, 4-hydroxy-5-methoxy-1-N-benzyloxycarbonylindoline, 6-hydroxy-7-methoxy-1-N-benzyloxycarbonylindoline, 5-methoxy-6-hydroxy-1-N-benzyloxycarbonylindoline, or 1-N-benzyloxycarbonylindoline.

4. The process according to claim 1, wherein said indole compound of the formula (II) is 5,6-dihydroxyindole, 6-hydroxyindole, 4-hydroxy-5-methoxyindole, 6-hydroxy-7-methoxyindole, 5-methoxy-6-hydroxyindole, or indole.

5. The process according to claim 1, wherein the pH of the solvent medium ranges from 5 to 7.

6. The process according to claim 1, wherein the hydrogen is molecular hydrogen at a low pressure.

7. The process according to claim 1, wherein the hydrogen donor is an olefinic hydrogen donor.

8. The process according to claim 1, wherein said hydrogenation catalyst is chromium, molybdenum, tungsten, platinum, palladium, rhodium, cobalt, nickel, ruthenium, oxides thereof, or combinations thereof.

9. The process according to claim 8, wherein said hydrogenation catalyst is palladium, Raney nickel, or another metal from the platinum group.

10. The process according to claim 1, wherein said hydrogenation catalyst is placed on neutral wood charcoal, neutral charcoal, neutral alumina, zeolites, or clays.

11. The process according to claim 1, wherein the solvent is an inert solvent, the inert solvent being a $C_1$–$C_4$ alcohol, a hydrocarbon, ethyl acetate, or dimethylformamide.

12. The process according to claim 11, wherein the solvent is ethanol or ethyl acetate.

13. The process according to claim 1, wherein the halogen atom is fluorine, chlorine, bromine, or iodine.

14. The process according to claim 8, wherein said hydrogenation catalyst is cobalt oxide, molybdenum oxide, or cobalt molybdate.

15. The process according to claim 7, wherein said olefinic hydrogen donor is cyclohexene, a substituted cyclohexene, 1,3-cyclohexadiene, or 1,4-cyclohexadiene.

16. The process according to claim 6, wherein said low pressure ranges from 1 to 5 atmospheres.

* * * * *